United States Patent
Richardson, Jr.

(10) Patent No.: US 11,272,908 B2
(45) Date of Patent: Mar. 15, 2022

(54) HANDHELD BIOPSY PUNCH PEN

(71) Applicant: Will Richardson, M.D., P.A., Fort Lauderdale, FL (US)

(72) Inventor: Willie Richardson, Jr., Wilton Manors, FL (US)

(73) Assignee: Will Richardson, M.D., P.A., Fort Lauderdale, FL (US)

( * ) Notice: Subject to any disclaimer, the term of this patent is extended or adjusted under 35 U.S.C. 154(b) by 119 days.

(21) Appl. No.: 16/681,815

(22) Filed: Nov. 12, 2019

(65) Prior Publication Data

US 2020/0146658 A1     May 14, 2020

Related U.S. Application Data

(60) Provisional application No. 62/760,022, filed on Nov. 12, 2018.

(51) Int. Cl.
    *A61B 10/02*         (2006.01)
    *A61B 17/3205*     (2006.01)

(52) U.S. Cl.
    CPC .... *A61B 10/0275* (2013.01); *A61B 17/32053* (2013.01); *A61B 2010/0208* (2013.01)

(58) Field of Classification Search
    CPC .......... A61B 10/0275; A61B 17/32053; A61B 2010/0208
    See application file for complete search history.

(56) References Cited

U.S. PATENT DOCUMENTS

| | | |
|---|---|---|
| 4,600,014 A | 7/1986 | Beraha |
| 4,699,154 A | 10/1987 | Lindgren |
| 5,025,797 A | 6/1991 | Baran |
| 5,146,921 A | 9/1992 | Terwilliger et al. |
| 5,827,199 A | 10/1998 | Alexander |
| 6,022,324 A | 2/2000 | Skinner |
| 7,775,989 B2 | 8/2010 | Nakao |
| 7,963,928 B2 | 6/2011 | Krause |
| 9,173,641 B2 | 11/2015 | Chudzik et al. |
| 9,259,210 B2 | 2/2016 | Lee et al. |
| 2004/0167429 A1* | 8/2004 | Roshdieh ........... A61B 10/0233 600/567 |
| 2004/0167430 A1 | 8/2004 | Roshdieh et al. |
| 2006/0116606 A1 | 6/2006 | Endo |
| 2007/0249960 A1 | 10/2007 | Williamson, IV |
| 2008/0214917 A1* | 9/2008 | Boecker ............. A61B 5/14532 600/347 |

* cited by examiner

*Primary Examiner* — Sean P Dougherty
(74) *Attorney, Agent, or Firm* — Mark C. Johnson; Johnson Dalal

(57) ABSTRACT

A handheld biopsy punch pen assembly with a first sampling housing selectively removably couplable to a body of the assembly and having a skin puncturing assembly disposed therein that includes a distal tip and with at least one blade member disposed thereon. The assembly includes a spring-loaded pen assembly operably configured to have a loaded position with the distal tip of the skin puncturing assembly recessed, a sampling position with the distal tip projecting outwardly away from the lower end of the first sampling housing for sampling of a user's skin and with the distal end the plunger member directly coupled to the skin puncturing assembly, and a retracted position with the distal tip projecting outwardly away from, and disposed a length away from, the lower end of the first sampling housing and with the distal end the plunger member uncoupled to the skin puncturing assembly.

17 Claims, 6 Drawing Sheets

HANDHELD BIOPSY PUNCH PEN

CROSS-REFERENCE TO RELATED APPLICATION

This application claims priority to U.S. Provisional Patent Application No. 62/760,022, filed Nov. 15, 2018, the entirety of the same is incorporated herein by reference.

FIELD OF THE INVENTION

The present invention relates generally to biopsy pens, and, more particularly, relates to a handheld biopsy pen operably configured to receive a skin sample from a user.

BACKGROUND OF THE INVENTION

A biopsy punch is a device operably configured to take minimally invasive and small skin or other tissue samples quickly. The biopsy punch may be a handheld and pencil-shaped instrument with a slender, pencil-like body (also referred to as a "punch pen"). The punch pen is typically lightweight with a hollow, circular, stainless steel, cutting tip. The punch pens may be employed for dermatology, therapeutics, cosmetic procedures, and for diagnosing and treating various medical conditions. Punch pens have also found their way into the research world and are frequently used in a variety of applications that include, but are not limited to, electrophysiology, bio-pharmacology, anti-aging research, forensic sampling, microfluidics/lab, and/or plant and medical genomics.

Punch pens may include a variety of different tip sizes, ranging in size from approximately 0.15 to 3.0 mm. Punch pens may also be disposable or for limited reuse. Some punch pens may be constructed of stainless steel or another material. Some punch pens utilize a retractable cutting cannula. Some known punch pens are generally easy to operate, but also have a variety of disadvantages. For example, these punch pens do not adequately preserve the tissue samples, resulting degraded samples after use. Additionally, these punch pens also do not effectively or efficiently obtain tissue samples from a user.

Therefore, a need exists to overcome the problems with the prior art as discussed above.

SUMMARY OF THE INVENTION

The invention provides a handheld biopsy punch pen that overcomes the hereinafore-mentioned disadvantages of the heretofore-known devices and methods of this general type and that effectively, safely, and efficiently receive, store, and transport a person's skin and/or tissue sample.

With the foregoing and other objects in view, there is provided, in accordance with the invention, a handheld biopsy punch pen assembly have includes a handheld body with a sidewall having a first end defining a first body aperture, a second end opposing the first end of the body and defining a second body aperture, and defining and enclosing a body cavity. The handheld biopsy punch pen assembly also includes a first sampling housing having an upper end defining an upper aperture and with an upper cover selectively, removably, and directly coupled to the upper end and superimposed over the upper aperture, wherein the upper end selectively removably coupled to the second end of the sidewall. The first sampling housing also includes a lower end opposite the upper end of the first sampling housing and defining a lower aperture, the first sampling housing with a lower cover selectively, removably, and directly coupled to the lower end and superimposed over the lower aperture, wherein the first sampling housing, the upper cover, and the lower cover are configured to encapsulate and define a sampling cavity therein. The first sampling housing also includes a skin puncturing assembly disposed within the sampling cavity, with a distal tip, and with at least one blade member disposed thereon. The handheld biopsy punch pen assembly also includes a spring-loaded pen assembly having a plunger member partially disposed within the body cavity, with a head, and a distal end opposing the head of the plunger member, wherein the first end of the body interposes the head and the body cavity. The spring-loaded pen assembly is operably configured to have a loaded position along a plunger translation path with the upper end of the first sampling housing removably coupled to the second end of the sidewall of the body, a spring member surrounding a portion of the plunger member, and the distal tip of the skin puncturing assembly recessed within the sampling cavity. The spring-loaded pen assembly is also operably configured to have a sampling position along the plunger translation path with the distal tip projecting outwardly away from, and disposed a length away from, the lower end of the first sampling housing for sampling of a user's skin and with the distal end the plunger member directly coupled to the skin puncturing assembly. The spring-loaded pen assembly is also operably configured to have a retracted position along the plunger translation path with the distal tip projecting outwardly away from, and disposed a length away from, the lower end of the first sampling housing and with the distal end the plunger member uncoupled to the skin puncturing assembly.

Although the invention is illustrated and described herein as embodied in a handheld biopsy punch pen, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to a direction corresponding to an elongated direction of the plunger member of the punch pen, wherein "transverse" should be understood to mean a direction corresponding to a direction opposite of the longitudinal direction.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
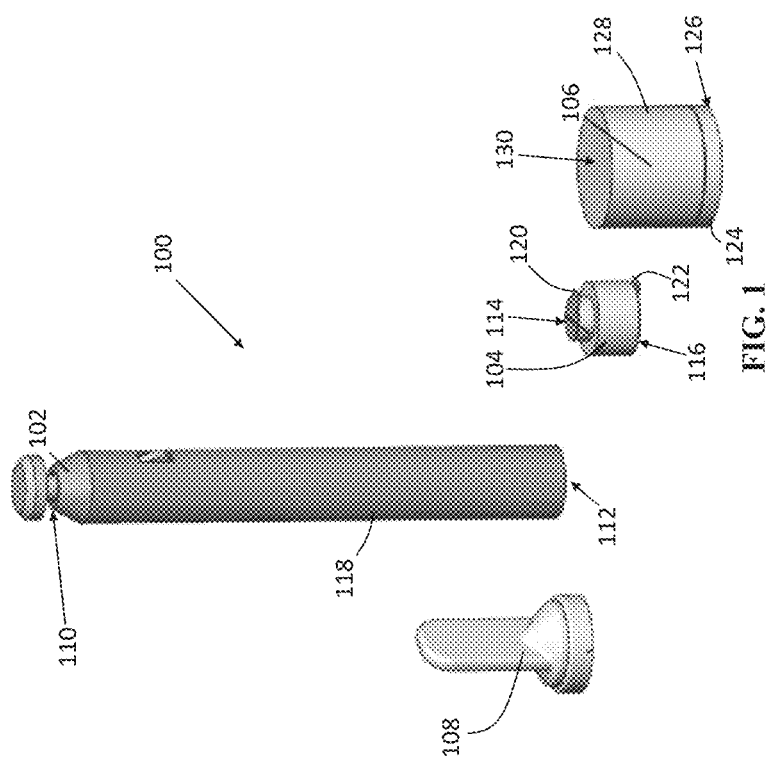
FIG. 1 is a perspective view of a handheld biopsy punch pen disassembled in accordance with one embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient handheld biopsy punch pen that is operably configured to selectively couple a tissue or skin sampling portion thereto and then, once the skin is sample, selectively uncouple the skin sampling portion from the punch pen for subsequent testing and without risk of degrading the tissue or skin sample.

Figure 2:
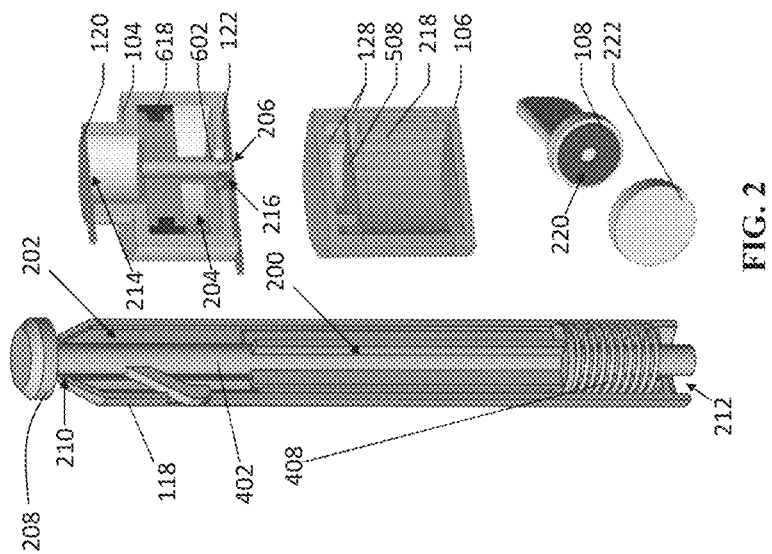
FIG. 2 is a perspective and partially cross-sectional view of the handheld biopsy punch pen in FIG. 1.

Referring now to FIG. 1, one embodiment of the present invention is shown in a perspective view, with the assembly in a disassembled configuration. FIG. 1, along with the other figures herein, show several advantageous features of the present invention, but, as will be described below, the invention can be provided in several shapes, sizes, combinations of features and components, and varying numbers and functions of the components. The first example of a handheld biopsy punch pen assembly 100, as shown in FIGS. 1-2, includes a handheld body 102 with a sidewall 118 having a first end 110 defining a first body aperture 210, a second end 112 opposing the first end 110 of the body 102 and defining a second body aperture 212, and defining and enclosing a body cavity 202. As used herein, the term "wall" is intended broadly to encompass continuous structures, as well as, separate structures that are coupled together so as to form a substantially continuous external surface.

Additionally, the assembly beneficially includes a first sampling housing 104 having an upper end 114 defining an upper aperture 214 and with an upper cover 120 selectively, removably, and directly coupled to the upper end 114 and superimposed over the upper aperture 214. The upper end 114 is beneficially selectively removably couplable to the second end 112 of the sidewall 118. The first sampling housing 104 also includes a lower end 116 opposite the upper end 114 of the first sampling housing 104 and defines a lower aperture 216. The first sampling housing 104 may also include a lower cover 122 selectively, removably, and directly coupled to the lower end 114 and be superimposed over the lower aperture 216 for selectively removal by the user when desired for use. The first sampling housing 104, the upper cover 120, and the lower cover 122 are configured to encapsulate and defining a sampling cavity 204 therein.

With reference to FIGS. 1-2, FIG. 4, and FIG. 6, a skin puncturing assembly 406 is disposed within the sampling cavity 204, wherein the skin puncturing assembly 406 includes a distal tip 206 and has at least one blade member 416 disposed thereon. Preferably, the inner surface 608 of a cannula member 602 includes a plurality of blade members 416a-n disposed thereon and having a cutting edge oriented in a longitudinal direction for removing portion(s) of a user's skin and/or tissue. Other orientations, however, are contemplated based on the design and application of the assembly 100.

The assembly 100 also includes a spring-loaded pen assembly 200 having a plunger member 402 partially disposed within the body cavity 202. The spring-loaded pen assembly 200 includes a head 414 and a distal end 418 opposing the head 414 of the plunger member 402. The first end 110 of the body 102 can be seen interposing the head 414 and the body cavity 202. The spring-loaded pen assembly 200 is operably configured to have various positions along a translation path, e.g., path 400 depicted in FIG. 4. The path 400 may be linear, curvilinear, or another path, but is preferably linear.

More specifically, the spring-loaded pen assembly 200 may have a loaded position (shown best in FIG. 3) along a plunger translation path 400 with the upper end 114 of the first sampling housing 104 removably coupled to the second end 112 of the sidewall 118 of the body 102, with a spring member 408 surrounding a portion of the plunger member 402, and the distal tip 206 of the skin puncturing assembly 406 recessed within the sampling cavity 204. Additionally, the spring-loaded pen assembly 200 may have a sampling position (shown best in FIG. 4) along the plunger translation path 400 with the distal tip 206 projecting outwardly away from, and disposed a length away from, the lower end 116 of the first sampling housing 104 for sampling of a user's skin and with the distal end 418 the plunger member 402 directly coupled to the skin puncturing assembly 406. The spring-loaded pen assembly 200 may also have a retracted position (shown best in FIG. 4) along the plunger translation path 400 with the distal tip 206 projecting outwardly away from, and disposed a length away from, the lower end 116 of the first sampling housing 104 and with the distal end 418 the plunger member 402 uncoupled to the skin puncturing assembly 406. The retract position beneficially permits the body 102 to be reused by the user, while being able to selectively remove the first sampling housing 104 from the body 102 of the assembly 100.

Additionally, the upper end 114 of the first sampling housing 104 may advantageously be selectively removably couplable to the second end 112 of the sidewall 118 in a threaded configuration. Further, the upper cover 120 and the lower cover 122 may be both of a metallic foil material. Additionally, the skin puncturing assembly 406 may have a head member 600 disposed, and operably configured to linearly and longitudinally translate, within the sampling cavity 204 and a cantilevered cannula member 602 projecting from the head member 600. As seen in the figures, the cantilevered cannula member 602 may have a distal opening 604 defined by the distal tip 206 of the skin puncturing assembly 406 and an enclosed channel 606 defined by an inner surface 608 of the cannula member 602 and spatially coupled to the distal opening 604, the inner surface 608 of the cannula member 602 having the least one blade member 416 disposed thereon.

The cantilevered cannula member 602 may beneficially have a distal opening 604 defined by the distal tip 206 of the skin puncturing assembly 406 and an enclosed channel 606 defined by an inner surface 608 of the cannula member 602 and spatially coupled to the distal opening 604. The inner surface 608 of the cannula member 602 may have the least one blade member 416 disposed thereon. The head member 600 may include an upper surface 610 defining an aperture 612 thereon and spatially coupled to the distal opening 604 defined by the distal tip 206, a lower surface 614 opposing the upper surface 610 of the head member 600, and a sidewall 616 separating the upper and lower surfaces 610, 614 of the head member 600. The sampling position may also include the distal end 418 the plunger member 402 directly coupled to the upper surface 610 of the head member 600 of the skin puncturing assembly 406.

As such, the present invention overcomes known disadvantages of those known devices and methods of this general type and that effectively and efficiently captures and retains a targeted skin sample of a user/patient for subsequent testing and/or evaluation. While this invention may be carried out by medical professionals, its functionality and ease of use beneficially enables it to be also carried out by the general public not necessarily familiar or experienced with medicine. Although the invention is illustrated and described herein as embodied in a handheld biopsy punch pen, it is, nevertheless, not intended to be limited to the details shown because various modifications and structural changes may be made therein without departing from the spirit of the invention. Additionally, well-known elements of exemplary embodiments of the invention will not be described in detail or will be omitted so as not to obscure the relevant details of the invention. To that end, while not affecting the asserted patentability of the present invention, similar handheld biopsy devices have been disclosed that include similar components and functionality to that of the device described herein, e.g., Williamson, I V, U.S. Patent Application Pub. No. 2007/0249960 and Roshdieh et al., U.S. Patent Application Pub. No. 2004/0167430, wherein said references are incorporated herein by reference for a background of the state of art.

The attached figures are incorporated in and form part of the specification, and serve to further illustrate various embodiments and explain various principles and advantages all in accordance with the present invention. Moreover, it is believed that the invention will be better understood from a consideration of the following description in conjunction with the drawing figures, in which like reference numerals are carried forward.

Figure 3:
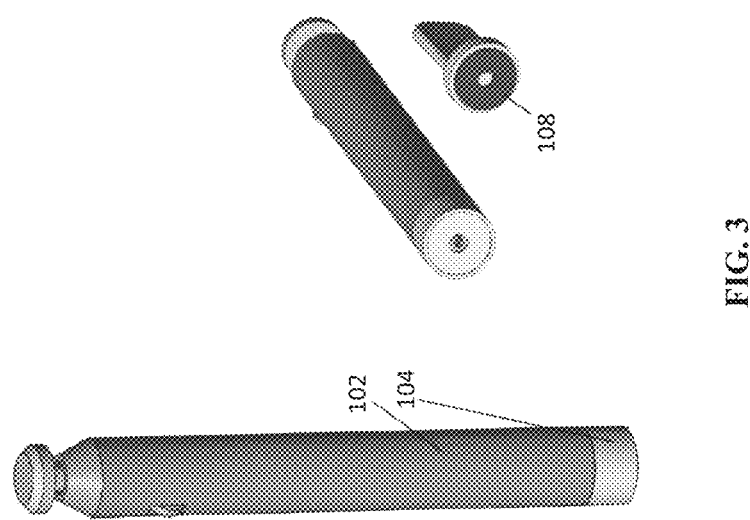
FIG. 3 is a perspective view of the handheld biopsy punch pen in FIG. 1 in an assembled configuration.
Figure 4:
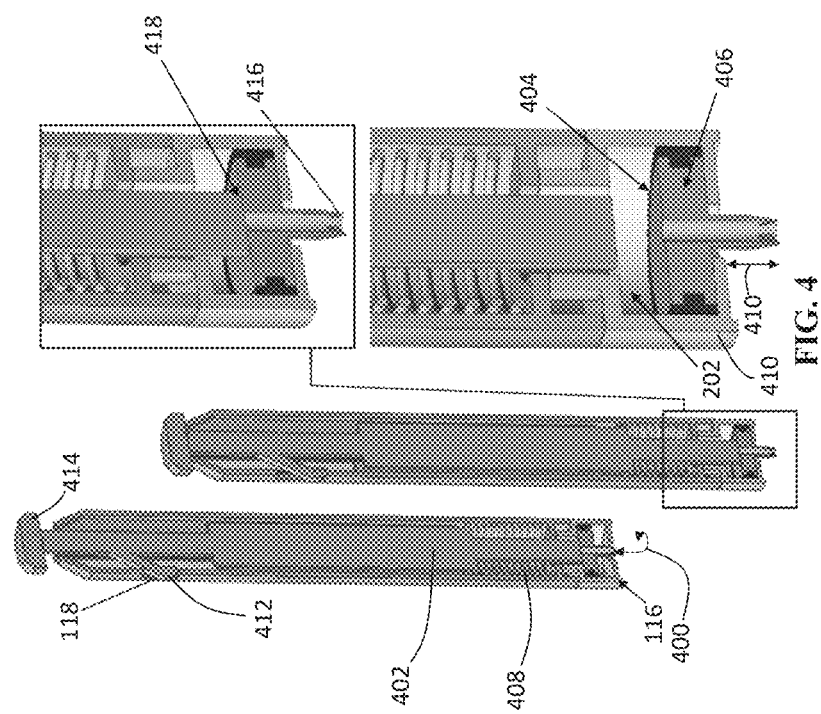
FIG. 4 depicts perspective, partially cross-sectional, and close-up views of the handheld biopsy punch pen in FIG. 2.
Figure 6:
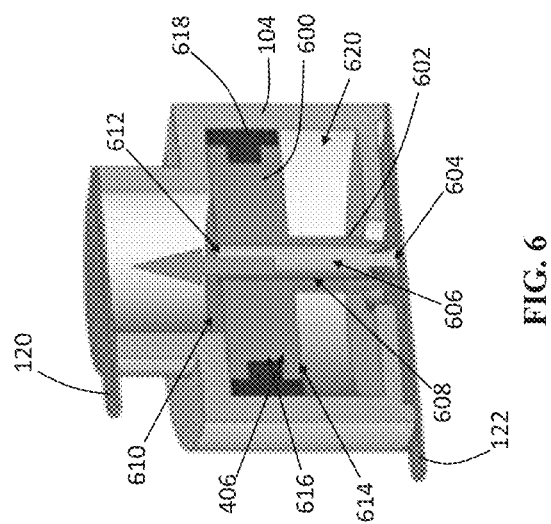
FIG. 6 is a cross-sectional view of a first sampling housing in accordance with one embodiment of the present invention.
Figure 5:
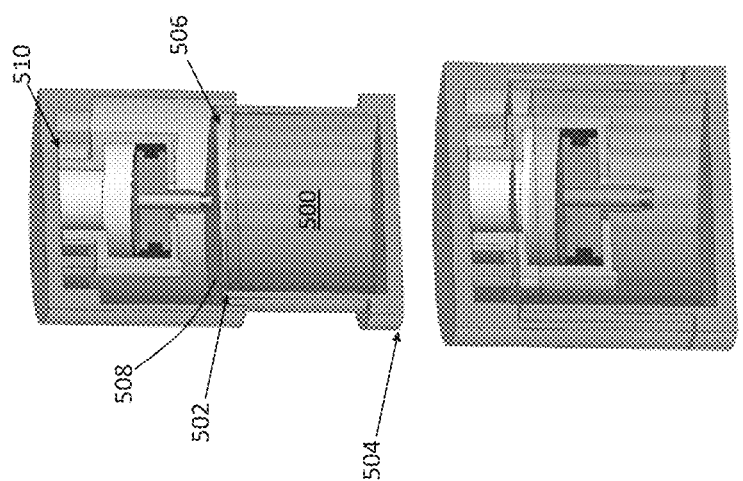
FIG. 5 is a cross-sectional view of a first sampling housing and a second sampling housing in accordance with one embodiment of the present invention.

Referring now to FIGS. 1-2, one embodiment of the present invention is shown in various views. FIGS. 1-2 shows several advantageous features of the present invention, but, as will be described below, the invention can be provided in several shapes, sizes, combinations of features and components, and varying numbers and functions of the components. The first example of a handheld biopsy punch pen 100, as shown in FIGS. 1-2, includes a handheld body 102, a first sampling housing 104, a spring-loaded biopsy pen assembly 200, a second sampling housing 106, and a patient skin marking tool 108. FIGS. 1-2 will also be described in conjunction with the process flow diagrams of FIGS. 3-5. Although FIG. 3-5 show a specific order of executing the process steps in an exemplary method of obtaining and storing a patient's skin sample with the herein described handheld punch pen biopsy assembly, the order of executing the steps may be changed relative to the order shown in certain embodiments. Also, two or more steps shown in succession may be executed concurrently or with partial concurrence in some embodiments. Certain steps may also be omitted in FIGS. 3-5 for the sake of brevity. In some embodiments, some or all of the process steps included in FIGS. 3-5 can be combined into a single process.

The handheld body 100 has a first end 110, a second end 112 opposing the first end of the body and defining and enclosing a body cavity 202. More specifically, the body may include a substantially enclosed sidewall that defines the body cavity, wherein the sidewall includes one or more apertures or slots thereon for enabling plunging or translation of the biopsy pen assembly. In one embodiment, the body may be of substantially rigid polymeric material, e.g., polystyrene. In other embodiments, other materials may be utilized, e.g., a metallic such as aluminum. The cavity may be shaped and sized as shown in the figures to accommodate portions or components of the biopsy pen assembly, but the body, which defines the body cavity, is preferably sized to be handheld.

The first sampling housing 104 may define a sampling cavity 204 encapsulated or enclosed therein. The first sampling housing includes an upper end and 114 a lower end 116 opposite the upper end of the first sampling housing, wherein the upper end of the first sampling housing is operably configured to be selectively removably couplable to the second end of the handheld body. In one embodiment, the coupling connection between the first sampling housing and the body may be through a threaded configuration. In other embodiments, the coupling configuration may be through a tongue-and-groove configuration, adhesive, or the like.

With reference to FIGS. 1-4, the first sampling housing may be sealed, preferably hermetically, using, for example, a foil material adhered on the upper and lower ends thereon. The first sampling housing may also house a distal tip 206 of the biopsy pen assembly to prevent inadvertent puncture of a user. As such, the sampling process may begin with placing the biopsy pen assembly in a loaded position along a plunger translation path (an exemplary path is shown in FIG. 4 with arrow 400) and coupling the first sampling housing to the second end of the body. When first sampling housing is engaged with the body, a portion of the body and/or the biopsy pen assembly may puncture the foil on the upper end of the first sampling housing and enable connection of a portion of the biopsy pen assembly, e.g., a distal end 400 of a plunger member 402, with a proximal end 404 of a skin puncturing assembly 406. In one embodiment, the connection between the distal end 400 and proximal end 404 may be effectuated through a male-female friction-fitted configuration. In other embodiments, the connection may be effectuated through adhesive or a tongue-and-groove configuration that enables locking between the two while in the loaded position and in the plunger translation path.

The spring-loaded biopsy pen assembly can be seen at least partially disposed within the body cavity. The head 208 of the assembly is disposed outside if the body cavity and is disposed for use or depression by the user. Said differently, the first end of the body interposes the head and the body cavity. The skin puncturing assembly includes the distal tip 206 may include a blade member disposed thereon for cutting the targeted area of a user's skin. When in the loaded position, the plunger member 402 may be biased with a spring member 408, i.e., the biopsy pen assembly may be "spring-loaded." When spring loaded, the plunger member, through the spring member, stores a potential energy operably configured to create a sufficient amount of force to puncture and sample a user's skin with the distal tip, e.g., 1-5 lbf. When in the loaded position, the skin puncturing assembly is also disposed within the sampling cavity, thereby the body of the device reusable and the skin puncturing assembly, namely the distal tip and blade being disposable or available for a one-time use for safety to the user.

After being loaded and having the first sampling housing coupled to the body, the user may mark the desired targeted sample area of the user's skin with the skin marking tool 108. Beneficially, an end of the marking tool 108 may include a marking area covered with, for example, ink, or another marking material. The marking area may be a size and/or shape that corresponds to the shape and/or size of the bottom end 116 of the first sampling housing so the user knows how and where to align the punch pen. Said another way, the outer perimeter of the marking area is substantially identical to that of the outer perimeter of the bottom end of the first sampling housing. Different marking areas may be utilized on different marking tools depending on the size of the sample desired and bottom end of the first sampling housing. Said differently, the patient skin marking tool 108 includes a lower surface 220 with an outer perimeter corresponding in shape and size to an outer perimeter of the lower end 116 of the first sampling housing 104. A cap 222 may be included that is selectively removably couplable to the patient skin marking tool 108 and operably configured to superimpose the lower surface 220 of the patient skin marking tool 108, thereby preserving the ink or other marking material disposed on the lower surface 220.

After or in lieu of the targeted skin area being marked, the user may place the biopsy pen assembly in the plunger translation path 400. In one embodiment, the plunger translation path is linear. In other embodiments, the plunger translation path is curvilinear. In preferred embodiments, the plunger translation path may be linear until it reaches or penetrates the skin of a user, at which point it then rotates to cause the blades of the distal tip to cut and retain the skin sample within a lumen defined on the distal tip. As such, the blade(s) on the distal tip and within the lumen may be disposed at an angled and transversely oriented configuration in relation to the rotation portion of the plunger translation path to effectively cut the user's skin. The plunger translation path may also be defined by using a cam-follower assembly disposed on the plunger member and the body.

Figure 7:
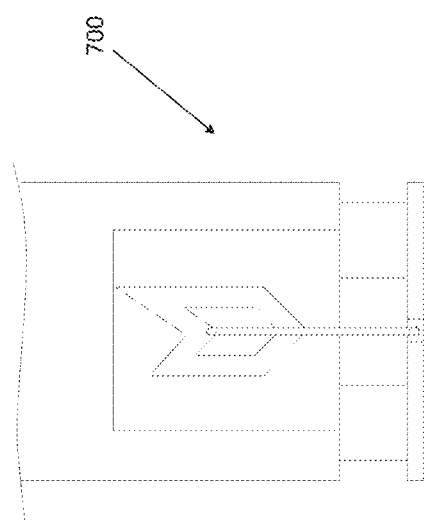
FIG. 7 is an elevational view of a cam shaft and channel utilized with a handheld biopsy punch pen in accordance with one embodiment of the present invention.

The plunger translation path also includes a sampling position with the distal tip disposed a length, e.g., length 410, away from the lower end of the first sampling housing for sampling of a user's skin. This length 410 may approximately 0.25-1.5 inches in one embodiment but may be outside of said range depending on the design constraints and applications. The length 410 may also be advantageously restricted by the internal sidewalls within the first sampling housing, i.e., the skin puncturing assembly 406 is limited in its translation because of the configuration of the internal sidewalls. To place the biopsy pen assembly in the plunger translation path 400, the user may depress a safety latch, e.g., latch 412. In other embodiments, the biopsy pen assembly may be placed in the plunger translation path 400 by depressing the head 208 to effectuate translation of an exemplary cam assembly 700 (shown in FIG. 7).

In one embodiment, the cam assembly 700 may include a cam arm, which may include a first end and a second end. In one embodiment, the first end of the cam arm may be mechanically coupled to the body. As such, the plunger member may be translated or placed in the plunger translation path using the cam assembly 700. More particularly, in one embodiment, the second end of the cam arm may be disposed within a channel defined in the plunger member. In one embodiment, the first end of the cam arm and the second end of the cam arm may define and be separated by a cam arm length. In one embodiment, the cam assembly may include a cyclical cam path. In one embodiment, the cyclical cam path may be defined by an outer surface of the plunger member. In one embodiment, the cam arm may be operably configured to revolve within the cyclical cam path. The above-described movement of the plunger member is likened to a movement found within conventional click-pens.

The skin puncturing assembly 406 may translate within the first sampling housing 104 during the plunger translation path. In one embodiment, the skin puncturing assembly 406 may include a gasket 618 disposed and surrounding thereon such that when the plunger member is retracted to the loaded position, the skin puncturing assembly 406 will remain at the bottom inside surface of the skin puncturing assembly 406. Said another way, the gasket 618 on the skin puncturing assembly 406 creates enough friction force to keep the skin puncturing assembly 406 at the bottom of the first sampling housing when the distal end of the plunger member is removed from the skin puncturing assembly 406. Said differently, the skin puncturing assembly 406 includes a polymeric gasket 618, e.g., of a natural rubber, coupled to the sidewall 616 of the head member 600 and directly coupled to an inner surface 620 of the first sampling housing 104.

In other embodiments, when the plunger member is retracted toward the loading position, the skin puncturing assembly 406 is retracted with it such that an inner sidewall of the skin puncturing assembly 406 prevents it from traveling further, thereby disposing the distal tip within the cavity of the skin puncturing assembly.

After removing the targeted area of a user's skin, the user will then remove the first sampling housing from the body. Beneficially, the first sampling housing may then be attached to the second sampling housing as shown best in FIG. 5. The second sampling housing defines a sample storing cavity 500 encapsulated therein. The cavity of the second sampling housing beneficially includes a skin preserving liquid, e.g., formalin, housed therein. The second sampling housing also includes an upper end 502 and a lower end opposite 504 the upper end 502. The upper end may include a foil disposed thereon for puncturing by the distal tip and/or the user. Said another way, the lower end of the first sampling housing is selectively removably coupled to the upper end of the second sampling housing to dispose the distal tip within the sample storing cavity or otherwise exposed to the skin preserving liquid for later evaluation by a medical professional. In one embodiment, the coupling of the first and second sampling housings are operably configured to couple together in a watertight and/or hermetically sealed configuration to preserve the integrity of the biopsied skin sample. To effectuate puncturing of the foil on the second sampling housing, the skin puncturing assembly is retained at the bottom end of the first sampling housing using the gasket (which may be a friction-inducing material, such as natural rubber), thereby keeping the distal tip disposed the length 410 away from the first sampling housing.

The second sampling housing 106 can also be seen including a lower portion 124 with a lower end 126, an upper portion 128 selectively removably coupled to the lower portion 124 in a watertight configuration and with an upper end 130 opposite the lower end 126 of the second sampling housing 106, wherein the lower portion 124 defining a sample storing cavity 500 with a skin preserving liquid therein. The lower portion 124 of the second sampling housing 106 can be seen having an upper end 502 defining an upper aperture 506 and with an upper cover 508 selectively, removably, and directly coupled to the upper end 502 of the second sampling housing 106 and superimposed over the upper aperture 506 defined by the upper end 502 of the second sampling housing 106. Further, the upper cover 508 of the second sampling housing 106 may be a metallic foil material, or other material operably configured to be easily punctured by the distal tip 206. Further, the upper end 114 of the first sampling housing 104 may also be operably configured to be selectively removably couplable to an inside surface 510 of the upper portion 128 of the second sampling housing 106 in a threaded configuration.

As such, a home biopsy assembly has been disclosed that includes a spring-loaded plunger assembly with a barbed-portion disposed at a terminal end thereof for and disposed within a housing. The barbed-portion of the spring-loaded plunger is operably configured to discharge through a distal end of the housing, rotate, and obtain a skin sample from a patient/user. Thereafter, the barbed-portion is configured to be removed from the housing of the assembly and securely retained and stored within a separate container, possibly through breaking a foil thereon, with formalin or other preserving liquid that permits the skin sample to be submerged therein. The assembly may also include a patient skin marking tool specially design to mark the target area of a user where the punch pen is to obtain the skin sample.

Although a specific order of steps for utilizing the present invention has been disclosed and depicted, the order of executing the steps may be changed relative to the order shown in certain embodiments. Also, two or more steps shown in succession may be executed concurrently or with partial concurrence in some embodiments. Certain steps may also be omitted for the sake of brevity. In some embodiments, some or all of the process steps discussed or depicted herein can be combined into a single process.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A handheld biopsy punch pen assembly comprising:
   a handheld body with a sidewall having a first end defining a first body aperture, a second end opposing the first end of the body and defining a second body aperture, and defining and enclosing a body cavity;
   a first sampling housing having:
      an upper end defining an upper aperture and with an upper cover selectively, removably, and directly coupled to the upper end and superimposed over the upper aperture, the upper end selectively removably coupled to the second end of the sidewall;
      a lower end opposite the upper end of the first sampling housing and defining a lower aperture, the first sampling housing with a lower cover selectively, removably, and directly coupled to the lower end and superimposed over the lower aperture, the first sampling housing, the upper cover, and the lower cover encapsulating and defining a sampling cavity therein; and
      a skin puncturing assembly disposed within the sampling cavity, with a distal tip, and with at least one blade member disposed on the skin puncturing assembly; and
   a spring-loaded pen assembly having a plunger member partially disposed within the body cavity, with a head, and a distal end opposing the head of the plunger member, the first end of the body interposing the head and the body cavity, the spring-loaded pen assembly operably configured to have:
      a loaded position along a plunger translation path with the upper end of the first sampling housing removably coupled to the second end of the sidewall of the body, a spring member surrounding a portion of the plunger member, and the distal tip of the skin puncturing assembly recessed within the sampling cavity;
      a sampling position along the plunger translation path with the distal tip projecting outwardly away from, and disposed a length away from, the lower end of the first sampling housing for sampling of a user's skin and with the distal end the plunger member directly coupled to the skin puncturing assembly; and
      a retracted position along the plunger translation path with the distal tip projecting outwardly away from, and disposed a length away from, the lower end of the first sampling housing and with the distal end the plunger member uncoupled to the skin puncturing assembly.

2. The handheld biopsy punch pen assembly according to claim 1, further comprising:
a second sampling housing including a lower portion with a lower end, an upper portion selectively removably coupled to the lower portion in a watertight configuration and with an upper end opposite the lower end of the second sampling housing, the lower portion defining a sample storing cavity with a skin preserving liquid therein.

3. The handheld biopsy punch pen assembly according to claim 2, wherein the lower portion of the second sampling housing further comprises:
an upper end defining an upper aperture and with an upper cover selectively, removably, and directly coupled to the upper end of the second sampling housing and superimposed over the upper aperture defined by the upper end of the second sampling housing.

4. The handheld biopsy punch pen assembly according to claim 3, wherein:
the upper cover of the second sampling housing is of a metallic foil material.

5. The handheld biopsy punch pen assembly according to claim 4, wherein:
the upper end of the first sampling housing is operably configured to be selectively removably couplable to an inside surface of the upper portion of the second sampling housing in a threaded configuration.

6. The handheld biopsy punch pen assembly according to claim 1, wherein:
the upper end of the first sampling housing is selectively removably couplable to the second end of the sidewall in a threaded configuration.

7. The handheld biopsy punch pen assembly according to claim 1, wherein:
the upper cover and the lower cover are both of a metallic foil material.

8. The handheld biopsy punch pen assembly according to claim 1, wherein the skin puncturing assembly further comprises:
a head member disposed, and operably configured to linearly and longitudinally translate, within the sampling cavity; and
a cantilevered cannula member projecting from the head member.

9. The handheld biopsy punch pen assembly according to claim 8, wherein the cantilevered cannula member further comprises:
a distal opening defined by the distal tip of the skin puncturing assembly and an enclosed channel defined by an inner surface of the cannula member and spatially coupled to the distal opening, the inner surface of the cannula member having the least one blade member disposed thereon.

10. The handheld biopsy punch pen assembly according to claim 9, wherein the inner surface of the cannula member further comprises:
a plurality of blade members disposed thereon and having a cutting edge oriented in a longitudinal direction.

11. The handheld biopsy punch pen assembly according to claim 10, wherein the head member further comprises:
an upper surface defining an aperture thereon and spatially coupled to the distal opening defined by the distal tip, a lower surface opposing the upper surface of the head member, and a sidewall separating the upper and lower surfaces of the head member.

12. The handheld biopsy punch pen assembly according to claim 11, wherein the skin puncturing assembly further comprises
a polymeric gasket coupled to the sidewall of the head member and directly coupled to an inner surface of the first sampling housing.

13. The handheld biopsy punch pen assembly according to claim 11, wherein:
the sampling position includes the distal end the plunger member directly coupled to the upper surface of the head member of the skin puncturing assembly.

14. The handheld biopsy punch pen assembly according to claim 1, further comprising:
a patient skin marking tool with a lower surface with an outer perimeter corresponding in shape and size to an outer perimeter of the lower end of the first sampling housing.

15. The handheld biopsy punch pen assembly according to claim 14, further comprising:
a cap selectively removably couplable to the patient skin marking tool and operably configured to superimpose the lower surface of the patient skin marking tool.

16. A handheld biopsy punch pen assembly comprising:
a handheld body with a sidewall having a first end defining a first body aperture, a second end opposing the first end of the body and defining a second body aperture, and defining and enclosing a body cavity;
a first sampling housing having:
an upper end defining an upper aperture and with an upper cover selectively, removably, and directly coupled to the upper end and superimposed over the upper aperture, the upper end selectively removably coupled to the second end of the sidewall;
a lower end opposite the upper end of the first sampling housing and defining a lower aperture, the first sampling housing with a lower cover selectively, removably, and directly coupled to the lower end and superimposed over the lower aperture, the first sampling housing, the upper cover, and the lower cover encapsulating and defining a sampling cavity therein; and
a skin puncturing assembly disposed within the sampling cavity, with a distal tip, and with at least one blade member disposed on the skin puncturing assembly;
a second sampling housing including a lower portion with a lower end, an upper portion selectively removably coupled to the lower portion in a watertight configuration and with an upper end opposite the lower end of the second sampling housing, the lower portion defining a sample storing cavity with a skin preserving liquid therein; and
a spring-loaded pen assembly having a plunger member partially disposed within the body cavity, with a head, and a distal end opposing the head of the plunger member, the first end of the body interposing the head and the body cavity, the spring-loaded pen assembly operably configured to have:
a loaded position along a plunger translation path with the upper end of the first sampling housing removably coupled to the second end of the sidewall of the body, a spring member surrounding a portion of the plunger member, and the distal tip of the skin puncturing assembly recessed within the sampling cavity;

a sampling position along the plunger translation path with the distal tip projecting outwardly away from, and disposed a length away from, the lower end of the first sampling housing for sampling of a user's skin and with the distal end the plunger member directly coupled to the skin puncturing assembly; and a retracted position along the plunger translation path with the distal tip projecting outwardly away from, and disposed a length away from, the lower end of the first sampling housing and with the distal end the plunger member uncoupled to the skin puncturing assembly.

17. A handheld biopsy punch pen assembly comprising:

a handheld body with a sidewall having a first end defining a first body aperture, a second end opposing the first end of the body and defining a second body aperture, and defining and enclosing a body cavity;

a first sampling housing having:
  an upper end defining an upper aperture and with an upper cover selectively, removably, and directly coupled to the upper end and superimposed over the upper aperture, the upper end selectively removably coupled to the second end of the sidewall;
  a lower end opposite the upper end of the first sampling housing and defining a lower aperture, the first sampling housing with a lower cover selectively, removably, and directly coupled to the lower end and superimposed over the lower aperture, the first sampling housing, the upper cover, and the lower cover encapsulating and defining a sampling cavity therein; and
  a skin puncturing assembly disposed within the sampling cavity, with a distal tip, with at least one blade member, with a head member disposed, and operably configured to linearly and longitudinally translate, within the sampling cavity, and with a cantilevered cannula member projecting from the head member, the cantilevered cannula member having a distal opening defined by the distal tip of the skin puncturing assembly and an enclosed channel defined by an inner surface of the cannula member and spatially coupled to the distal opening, the inner surface of the cannula member having the least one blade member disposed thereon; and a spring-loaded pen assembly having a plunger member partially disposed within the body cavity, with a head, and a distal end opposing the head of the plunger member, the first end of the body interposing the head and the body cavity, the spring-loaded pen assembly operably configured to have:
  a loaded position along a plunger translation path with the upper end of the first sampling housing removably coupled to the second end of the sidewall of the body, a spring member surrounding a portion of the plunger member, and the distal tip of the skin puncturing assembly recessed within the sampling cavity;
  a sampling position along the plunger translation path with the distal tip projecting outwardly away from, and disposed a length away from, the lower end of the first sampling housing for sampling of a user's skin and with the distal end the plunger member directly coupled to the skin puncturing assembly; and
  a retracted position along the plunger translation path with the distal tip projecting outwardly away from, and disposed a length away from, the lower end of the first sampling housing and with the distal end the plunger member uncoupled to the skin puncturing assembly.

* * * * *